United States Patent [19]

Schafer

[11] 4,220,830

[45] Sep. 2, 1980

[54] HEARING AID WITH MODULATED SUPPRESSED CARRIER SIGNAL

[75] Inventor: Curtiss R. Schafer, Newtown, Conn.

[73] Assignee: Electro-Physical Research, Incorporated, Fort Lee, N.J.

[21] Appl. No.: 931,023

[22] Filed: Aug. 4, 1978

[51] Int. Cl.² ............................................ H04R 25/00
[52] U.S. Cl. .................................. 179/107 R; 332/44; 455/109
[58] Field of Search ............ 179/107 BC, 107 R, 1 R; 325/138, 329; 332/44

[56] References Cited

U.S. PATENT DOCUMENTS

| | | | |
|---|---|---|---|
| 2,373,569 | 4/1945 | Kannenberg | 332/44 |
| 3,238,472 | 3/1966 | Crompton-Couvela | 332/44 |
| 3,393,279 | 7/1968 | Flanagan | 179/107 R |
| 3,514,720 | 5/1970 | Roucache et al. | 332/43 |
| 3,811,098 | 5/1974 | Williams | 332/44 |
| 4,052,572 | 10/1977 | Schafer | 179/107 R |

Primary Examiner—Thomas W. Brown

[57] ABSTRACT

Disclosed hearing aids have circuits that produce a suppressed-carrier modulated signal and they include an electrode to be applied to the head of the user for coupling the suppressed-carrier modulated signal to the user's auditory cortex.

6 Claims, 5 Drawing Figures

HEARING AID WITH MODULATED SUPPRESSED CARRIER SIGNAL

The present invention relates to hearing aids.

In my U.S. Pat. No. 4,052,572 issued Oct. 4, 1977, there is disclosed a particular form of hearing aid that I call a "cortical hearing aid". In that device, a modulated carrier is coupled by an electrode to the auditory cortex of the user. That kind of hearing aid deviates fundamentally from electro-acoustic hearing aids. Certain individuals can "hear" when using my patented cortical hearing aid, whereas they could not hear with the aid of electro-acoustical devices. For many other individuals, the cortical hearing aid of my previous invention made a distinct improvement over electro-acoustic hearing aids.

SUMMARY OF THE INVENTION

An object of the present invention resides in the provision of a new and improved cortical hearing aid. In the present invention, a carrier signal is modulated in a way that produces a suppressed-carrier modulated signal. Such signals have long been known and many of their advantages have been recognized. However it has also been understood that such a signal is only to be used in transmission, that a carrier is to be added or restored to the received signal before the detection process. An important advantage of suppressed-carrier signals used in radio transmission is that the amount of energy in the transmission is greatly reduced as compared to transmission of ordinary amplitude-modulated carriers.

The present invention departs from the traditional use of suppressed-carrier technology. Suppressed-carrier signals are normally transmitted to specially designed receivers. These include detectors in which a locally introduced carrier is utilized. Here, the suppressed-carrier modulated signal is used directly in a cortical hearing aid, without addition of a carrier in a detector. As in my previous cortical hearing aid, the modulated carrier is coupled into the user's head by means of an applied electrode. In contrast to the ordinary amplitude-modulated signal in which the full measure of carrier energy is maintained at all times, here the amount of carrier-frequency energy that is developed and coupled into the user's head is greatly conserved. Whereas an ordinary amplitude-modulated signal includes a carrier and two sidebands, suppression of the carrier eliminates the energy represented by the carrier. When there is little audio signal, or none at all, there is little energy or none in the suppressed-carrier modulated signal.

The present invention resides in part on the discovery that suppressed-carrier audio modulated signals can be utilized directly in the cortical hearing process, with notable success. Conservation of energy in a hearing aid is recognized as being of considerable importance, inasmuch as hearing aids are highly portable and depend on batteries for energization. Reduced energy requirements makes possible smaller and longer-life batteries.

With ordinary amplitude-modulated signals, the magnitude of the carrier imposes a virtual limit on the modulation that can be transmitted. Distortion becomes prominent when 100% modulation is exceeded. I have found that a suppressed-carrier modulated signal can be used in a cortical hearing aid with 50% and even 100% overmodulation and without undue distortion.

In a cortical hearing aid, it is of practical importance to use a carrier whose frequency is extremely low as compared to amplitude-modulated signals used in radio transmission. A carrier frequency in the range of about 15 kHz to 60 kHz is optimum. This creates filtering problems in the modulator of a conventional amplitude-modulation system, for maintaining separation between the audio and carrier frequencies, in a cortical hearing aid. This is because the upper limit (e.g. 10 kHz) of the audio-frequency spectrum used as modulation approaches the lower range of the optimum carrier-frequency range. Particularly in the suppressed-carrier system of the illustrative embodiments of the invention (detailed below) no problem or difficulty arises concerning separation of the audio and carrier frequencies in the modulator. In the preferred illustrative embodiment of the invention, the modulator has rectifiers that short-circuit the audio signal in alternate half-waves of the carrier signal.

Detection or demodulation of a suppressed-carrier signal without first re-introducing the carrier (as is customary in suppressed-carrier radio transmission) has the well-known effect of doubling the frequency of the original audio signal. No such frequency-doubling effect was observed in actual use of the novel suppressed-carrier cortical hearing aid.

The nature of the invention and the foregoing and others of its novel features and advantages will be more fully appreciated from the following detailed description of the illustrative embodiments, which are shown in the accompanying drawing.

THE ILLUSTRATIVE EMBODIMENTS

Figure 1:
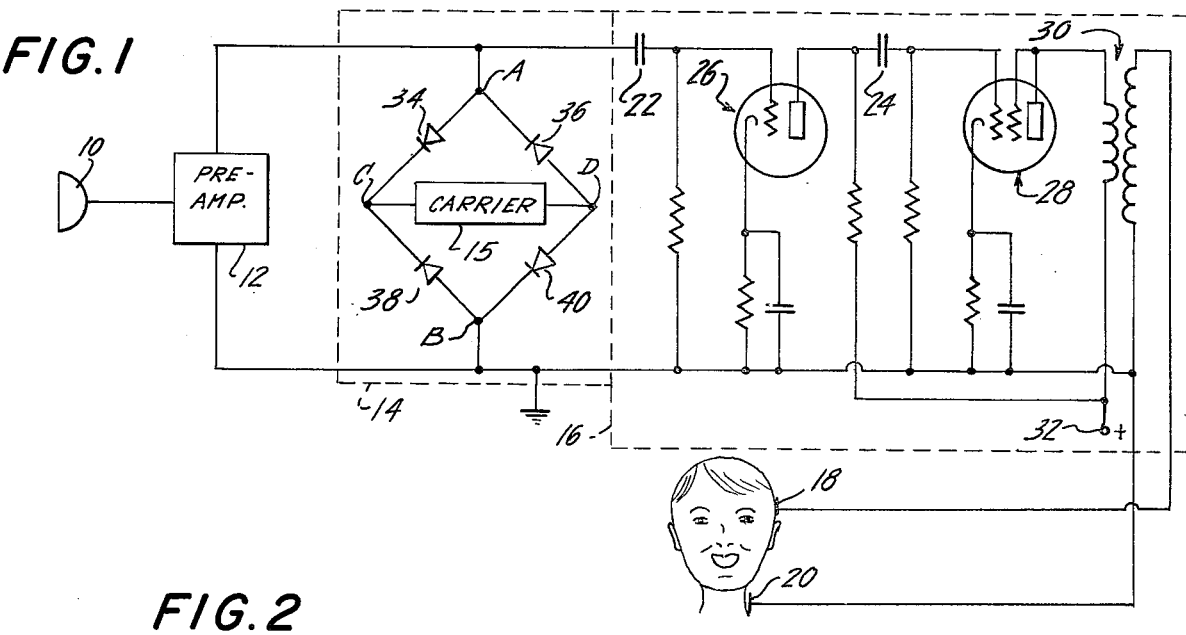
FIG. 1 is a block diagram including some circuit details, showing the presently preferred embodiment of a suppressed-carrier cortical hearing aid embodying features of the invention.

In FIG. 1, a microphone 10 connected to pre-amplifier 12 supplies a spectrum of audio frequencies such as music and speech to terminals A and B of a suppressed-carrier modulator 14. A carrier signal source 15 is connected to terminals C and D of the modulator. The suppressed-carrier modulated signal is coupled by amplifier 16 to electrodes 18 and 20 on the user.

Electrode 18 is a metal element that is covered with a thin layer of plastic insulation to provide an impedance that makes the device essentially a constant-current source and thus largely independent of the electrical properties of the patient's head. In an example it is a disc of about one-inch diameter. It is placed against the user's head at a place chosen by the user for optimum effect, usually at a spot forward and above the ear canal and to the rear of the temple. Electrode 20 which is not insulated may be of any size and proportion and connected to the user at any place, as at the neck. The apparatus described above is effective for a carrier frequency of 40 kHz, in an example. There is usually a significant amount of metal in the apparatus, serving as a shield to suppress radiation, connected to the common ground of the circuit. Electrode 20 provides a common potential for the user and that ground.

Amplifier 16 may be of any suitable form. In a successfully operated example, it includes input and interstage coupling capacitors 22 and 24 and two vacuum-tube stages 26 and 28 of amplification. Step-up output transformer 30 having a ratio of 2½:1 or 3:1 for example has its primary connected between the positive terminal of the direct-current supply and the anode of the last amplifier stage, and the secondary has one terminal connected to electrode 18. The other output-winding terminal is grounded and connected to electrode 20 and to the negative d-c terminal.

Modulator 14 is a four-diode bridge having the cathodes of two diodes 34 and 38 connected to carrier-source terminal C and having anodes of two diodes 36 and 40 connected to carrier-source terminal D. The anode of diode 34 is connected at terminal A to the cathode of diode 36, and the anode of diode 38 is connected at terminal B to the cathode of diode 40. Terminals A and B are input terminals from audio frequency source 10, 12 and terminals A and B are output terminals as well. This is because the diode bridge is biased into conduction and acts as a short-circuit during alternate half-cycles of the carrier signal, and during the remaining opposite half-cycles of the carrier the diodes are reverse-biased so that the audio signal is transmitted to amplifier 16 during alternate half-wave intervals of the carrier.

Figure 3A:
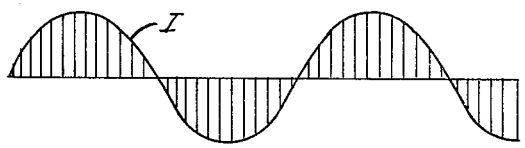
FIGS. 3A–3C show waveforms representative of the operation of the apparatus of FIG. 1.
Figure 3B:
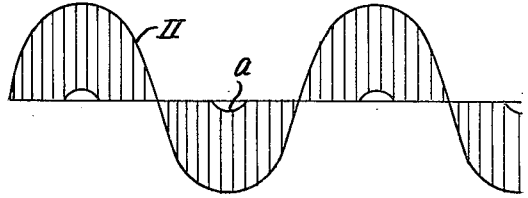
Figure 3C:
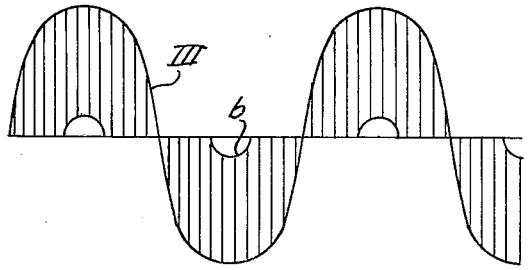

FIGS. 3A, 3B and 3C are diagrammatic representations of the operation of the apparatus of FIG. 1, approximately as they would appear on an oscilloscope. In FIG. 3A the peak value of a single tone of the audio input (represented by a sine wave) is equal to the peak value of the carrier, representing 100% modulation. FIGS. 3B and 3C represent 150% and 200% modulation, respectively.

The modulator operates to produce a suppressed-carrier modulated signal. At zero audio input, there is no output. At all levels of audio signal up to 100% modulation, the output is almost strictly proportional to the audio signal. The degree of approximation is related to the behavior of the diodes at fractional voltages. At audio voltages exceeding the carrier, the modulated signal output continues to rise with comparatively little resulting distortion in contrast to conventional amplitude-modulation where the carrier is not suppressed.

A modulator of the form in FIG. 1 was operated using two sine-wave signal generators connected as shown, to develop the information represented in FIGS. 3A, 3B and 3C. A carrier of 10 volts at 40 kHz was used with an audio signal of varied frequencies in the range 50 Hz to 10 kHz at voltages of zero to 21 volts. Audio signals involving spectrums of frequencies present in speech and music were also applied to the modulator and, with amplification, the electrodes applied as described produced the sensation of hearing, at normal frequencies. The estimated peak amplitude of the signal at the electrodes was of the order of 500 volts.

Clearly, many of the physical details of the illustrated circuit are optional. Vacuum-tube amplifiers may be replaced by appropriate transistors and integrated circuit types. Diodes may be replaced by transistor or other rectifiers. And while a bridge rectifier is shown and has many distinctive advantages as the modulator, other circuit arrangements can be used such as those involving a rectifier-and-transformer circuit having the abovedescribed performance characteristics. An adjustable capacitor may be connected across either winding of transformer 30 and tuned for resonance, for improved efficiency. A diode in series with the connection to electrode 18 improves word discrimination for some deaf people. Thus various changes and additions to the apparatus are envisioned.

Figure 2:
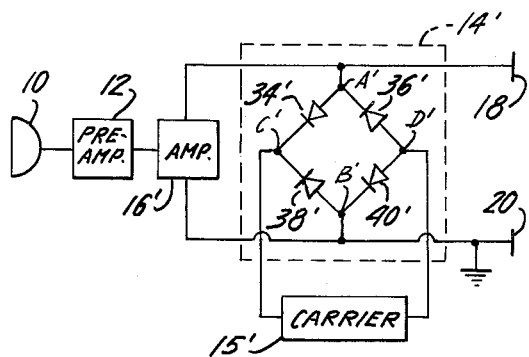
FIG. 2 shows a modification of FIG. 1.

FIG. 2 illustrates a modification of FIG. 1. The parts 10, 12, 18 and 20 in FIG. 2 are the same as those in FIG. 1. The primed parts are slightly different, due to insertion of amplifier 16' ahead of the modulator 14' rather than following the modulator as in FIG. 1. Higher signal levels are involved at the modulator in the system of FIG. 2. The operation and characteristics of FIG. 2 are otherwise the same as those of FIG. 1.

In the light of the foregoing, it is apparent that the disclosed invention is amenable to a wide variety of implementation, and that modifications and additions may be introduced by those skilled in the art. Consequently the invention should be construed broadly in accordance with its full spirit and scope.

What is claimed is:

1. A hearing aid including a source of audio signals representing a spectrum of the sounds to be heard, a carrier-frequency signal source, a suppressed-carrier modulator having input couplings to said audio signal source and to said carrier-frequency signal source and having output signal means at which a modulated suppressed-carrier signal appears, and means for impressing the modulated suppressed-carrier output signal of said modulator on the person of the user, said last-named means including at least an electrode adapted to bear against the user's head.

2. A hearing aid as in claim 1, wherein said suppressed-carrier modulator includes rectifying means arranged to effect transmission of the audio signals to the output during alternate half-waves of the carrier signal and to suppress such transmission during the remaining alternate half-waves of the carrier signal.

3. A hearing aid as in claim 1, wherein the audio signal source is coupled to said output signal means, and wherein said modulator includes rectifying means arranged to short-circuit the audio signal during alternate half-cycles of the carrier signal.

4. A hearing aid as in claim 1, wherein said modulator includes a bridge rectifier having four rectifiers each having an anode and a cathode, said rectifiers including first and second rectifiers having their anodes joined to each other and to one terminal of the carrier signal source, and third and fourth rectifiers having their cathodes joined to each other and to another terminal of the carrier signal source, the modulator having first and second output terminals joined to the audio signal source, the anode of the third rectifier and the cathode of the first rectifier being connected together and forming said first output terminal and the anode of the fourth rectifier and the cathode of the second rectifier being connected together and forming said second output terminal.

5. A hearing aid as in claim 1, wherein the carrier frequency is in the range of about 15 kHz to 60 kHz.

6. A hearing aid as in claim 4, wherein the carrier frequency is in the range of about 15 kHz to 60 kHz.

* * * * *